United States Patent [19]

Togo

[11] 4,091,814
[45] May 30, 1978

[54] LASER OPTICAL APPARATUS FOR OPERATION UNDER A MICROSCOPE

[75] Inventor: Takashi Togo, Tokyo, Japan

[73] Assignee: Mochida Pharmaceutical Co., Ltd., Kamiya, Japan

[21] Appl. No.: 777,417

[22] Filed: Mar. 14, 1977

[30] Foreign Application Priority Data

Mar. 15, 1976 Japan .................................. 51-27041

[51] Int. Cl.² ............................................ A61B 17/36
[52] U.S. Cl. ................................................ 128/303.1
[58] Field of Search ........................... 128/303.1, 395; 331/94.5

[56] References Cited

U.S. PATENT DOCUMENTS

| 3,348,547 | 10/1967 | Kavanagh | 128/395 |
|---|---|---|---|
| 3,533,707 | 10/1970 | Weiss | 128/395 UX |
| 3,653,384 | 4/1972 | Swope | 128/303.1 |
| 3,670,260 | 6/1972 | Koester et al. | 331/94.5 |
| 3,828,788 | 8/1974 | Kranov et al. | 128/303.1 |
| 3,910,276 | 10/1975 | Polanyi et al. | 128/303.1 |

*Primary Examiner*—Lawrence W. Trapp

[57] ABSTRACT

A laser optical apparatus for operation under a microscope comprises: a laser beam introducing 45° reflector arranged between two optical axes so as not to impair the range of vision frontwardly of a binocular telescope for operation, a parabolic mirror with a surface displaced from an axis for condensing introduced beams of laser and serving as an objective lens of the microscope, a plane reflector driven by motors to direct the condensed beams of laser and an optical axis of the microscope, and a maneuvering mechanism including a stick for operating said motor.

4 Claims, 4 Drawing Figures

LASER OPTICAL APPARATUS FOR OPERATION UNDER A MICROSCOPE

BACKGROUND OF THE INVENTION

The present invention relates to an optical apparatus used for a laser device for operation.

A laser knife for medical use condenses rays of laser of high output, for example, such as rays of $CO_2$ laser, and, by utilization of high temperatures then produced, vaporizes or solidifies a composition composed of protein or the like to effect operation. Since such laser knife for medical use possesses several advantages noted below, it is now increasingly used in field of surgical treatment.

(1) It offers styptic effects.
(2) Micro-surgery can be effected.
(3) Influence on those other than the affected part is minimal.
(4) Non-contact surgery can be effected.

In view of further advantages such that the diameter of the condensed beam of laser is very small and that the rays of laser may be introduced by the optical system into a deep part in a state of non-contact, micro-surgery laser operating apparatus, which is safety and easy in handling, has been demanded in the fields of cranial nerve surgery, otorhynoloaryngologist, and obstetrician, who must operate the deep part of the body.

To fulfill such demands, a few processes have been proposed lately. A first process is that rays of laser condensed by an infrared ray transmission lens are introduced to the affected part by a plane reflector fixed frontwardly of an objective lens of the microscope, and the sight of the laser beam is adjusted by moving the entire microscope up and down, right and left, and back and forth.

A second process is that rays of laser condensed by an infrared ray transmission lens are introduced to the affected part by a light introducing 45° reflector, which is designed so that it can be moved slightly in front of an objective lens of the microscope, and the sight of the laser beam is adjusted by varying an angle of the 45° reflector. This process is described in detail in Japanese Patent Laid-Open No. 8085/1974, entitled "Stereoscopic Laser Endoscope".

However, according to the above-described two processes, the rays of laser are commonly condensed by the lens and therefore, they are unavoidably suffered from out-of-focus of the condensed spot resulting from a slight transmission loss of the rays of laser and spherical aberration. Also, in the first process, in which the entire microscope is moved, there poses problems such that it is difficult to effect fine or slight movement if manual operation is employed, and that a large apparatus must be used if power operation is employed. Even in the second process, in spite of the fact that a mechanism, by which the angle of the introducing 45° reflector positioned in front of the objective lens is varied without impairing the range of field through an eyepiece, becomes complicated, it was impossible to allow the 45° reflector to effect its elevation movement and horizontal rotation in a completely independent manner when the reflector is shaked thereabout. This means that the sight of a laser spot cannot smoothly be adjusted to the target position by operating a single stick (a maneuvering lever). For example, it poses a problem such that even when the stick is moved laterally, the laser spot will move not only laterally but vertically.

SUMMARY OF THE INVENTION

It is therefore an object of the present invention to provide a laser optical apparatus for operation under a microscope which can minimize loss of rays of laser, produce no put-of-focus of the condensed spot, and afford a good maneuverability.

This and other objects have been attained by the laser optical apparatus for operation under a microscope according to the present invention, which comprises a laser beam introducing 45° reflector arranged between two optical axes so as not to impair the range of vision frontwardly of a binocular telescope for operation, a parabolic mirror with a surface displaced from an axis for condensing introduced beams of laser and serving as an objective lens of the microscope, a plane reflector driven by motors to direct the condensed beams of laser and an optical axis of the microscope, and a maneuvering mechanism including a stick for operating said motors.

In accordance with the laser optical apparatus for operation under a microscope of the present invention, the introduced laser beams are condensed by the parabolic mirror with a surface displaced from an axis, and for this reason, the loss of rays of laser can be minimized and the out-of-focus of the condensed laser beam and the optical axis of the microscope may be directed towards the target by means of the plane reflector driven by the motors through the operation of the operating stick, and hence, the laser optical apparatus for operation under a microscope, which is excellent in maneuverability, may be provided.

DESCRIPTION OF THE PREFERRED EMBODIMENTS

An embodiment of the present invention will now be described in detail with reference to the accompanying drawings.

Figure 1:
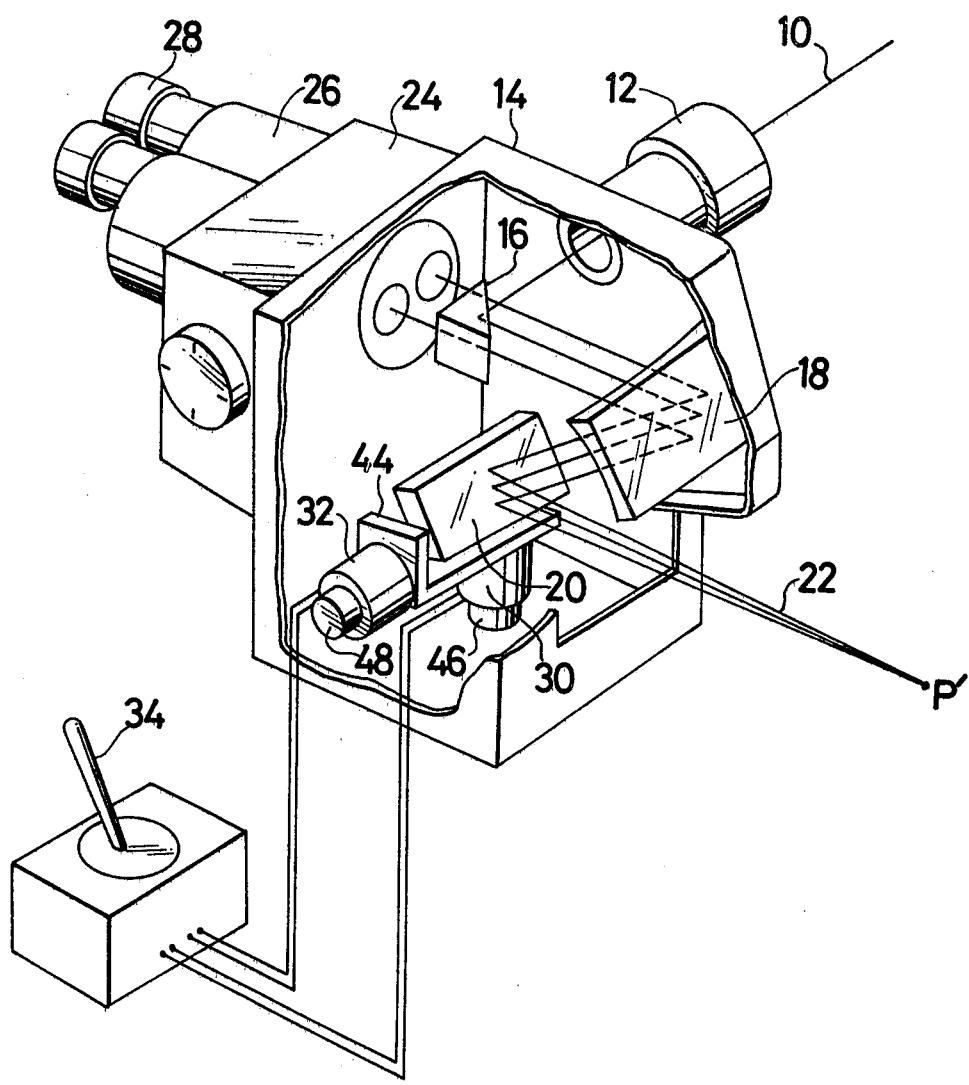
FIG. 1 is a perspective view showing one embodiment of a laser optical apparatus for operation under a microscope in accordance with the present invention.
Figure 2:
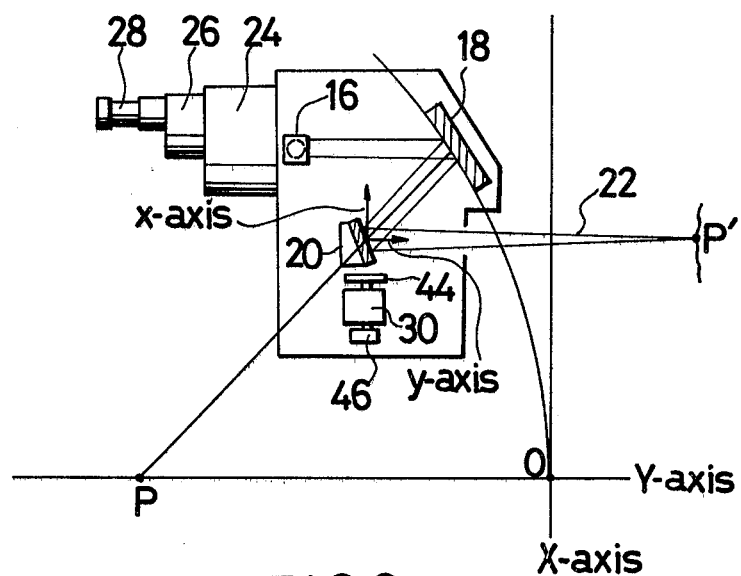
FIG. 2 is a side view in section of the apparatus shown in FIG. 1.
Figure 3:
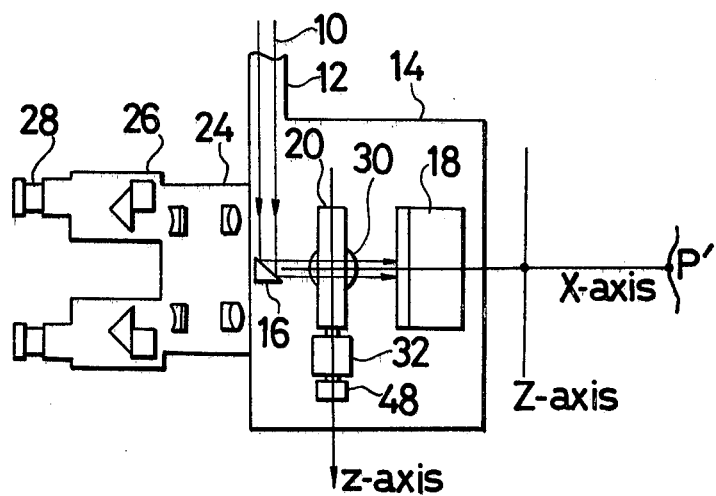
FIG. 3 is a plan view in section of the apparatus shown in FIG. 1.

FIG. 1 is a perspective view showing one embodiment of a laser optical apparatus for operation under a microscope in accordance with the present invention; FIG. 2 is a side view in section thereof, and FIG. 3 is a plan view in section of the same. Rays of laser 10 generated by a laser generator (not shown) enter a housing 14 through a laser ray introducing portion 12 and are reflected by a 45° reflector 16 and then condensed by a parabolic mirror 18 with a surface displaced from an axis, and the rays are then reflected by a plane mirror 20 towards the outside and incident on the affected part P'. Visible rays of light 22 from the affected part P' are reflected by the plane mirror 20 and formed into parallel rays of light by the parabolic mirror 18, and the rays of light pass by the opposite sides of the 45° reflector 16 into a magnification varying optical system 24. In a prism system 26, an inverted image is formed into an erect image and the affected part is observed by an eyepiece 28. The magnification varying optical system 24 serves to vary the magnification of the microscope while maintaining a working distance in constant.

The parabolic mirror 18 with a surface displaced from an axis is a mirror of which reflection surface is a partial surface displaced from main axis (axis-Y) of parabolic surface formed when a parabola taking an original point O with a focal point at P in the X-Y plane in FIG. 2 is rotated about the axis-Y.

Such a parabolic mirror has already been used for an astronomical telescope or the like, which is easily available. The parabolic mirror 18 reflectes rays of light incident in parallel to the main axis and condenses them at the focal point with no-aberration. Since the rule of reflection is established irrespective of wavelength of light, no aberration is produced with respect both to rays of $CO_2$ laser having the wavelength of 10.6 $\mu$ and to visible rays of light for observation.

A condenser lens used in an optical system, which requires exact registration of the focal position of the observation optical system with the focal position of rays of $CO_2$ laser as in the present apparatus, need to have an accurate focal distance as specified in design. However, since conventional focal distance measuring apparatus by means of visual light cannot be used for infrared ray of 10.6 $\mu$, it is impossible to verify and correct the focal distance in the stage of polishing step. It was therefore, necessary to produce several different lenses to select one closest to the specification for user or to incorporate a complicated lens fine movement focus control mechanism into the apparatus. It is noted that parabolic mirror with a surface displaced from an axis in preferably utilized to provide a laser optical apparatus for operation under a microscope, which is safety and simple in construction.

Rays of $CO_2$ laser introduced from the outside advance parallel to the main axis with the aid of the 45° reflector, which is positioned in the midst of a binocular optical system and secured to a position not to shut off rays of visible light for observation as described previously, are reflected and condensed by the parabolic mirror 18 and reflected by the plane reflector 20, and then condensed at pont P' which is in surface symmetry with the original focal point P. As a consequence, even if the plane reflector 20 is shaked, only the point P' will move whereas the focal point P will not change its position. Therefore, the rays of light from the moving point P' is always incident on the parabolic mirror 18 as if it comes out of the fixed point P. When the parabolic mirror 18 is moved to move the condensed point P' of beams of $CO_2$ laser, the condition where the beams of $CO_2$ laser are allowed to make incidence thereof parallel to the main axis fails to be satisfied to produce an aberration in the focal point of the laser beam and the observed image. In the laser optical apparatus for operation under a microscope according to the present invention, it is designed so that the parabolic mirror 18 with a surface displaced from an axis is fixed but the plan reflector 20 is movable, whereby the disadvantages noted above may be eliminated.

In accordance with one embodiment of the present invention, the plane reflector 20 is mounted on a rotational shaft of a servo-motor 32 mounted on a vertical member of an L-shaped supporting bed 44, which has a horizontal member mounted on a rotational shaft of a servo-motor 30. A stick 34, which controls signals to the servo-motors, may be maneuvered to rotate the plane reflector 20 about the vertical axis by means of the servo-motor 30 and about the horizontal axis by means of the servo-motor 32.

Figure 4:
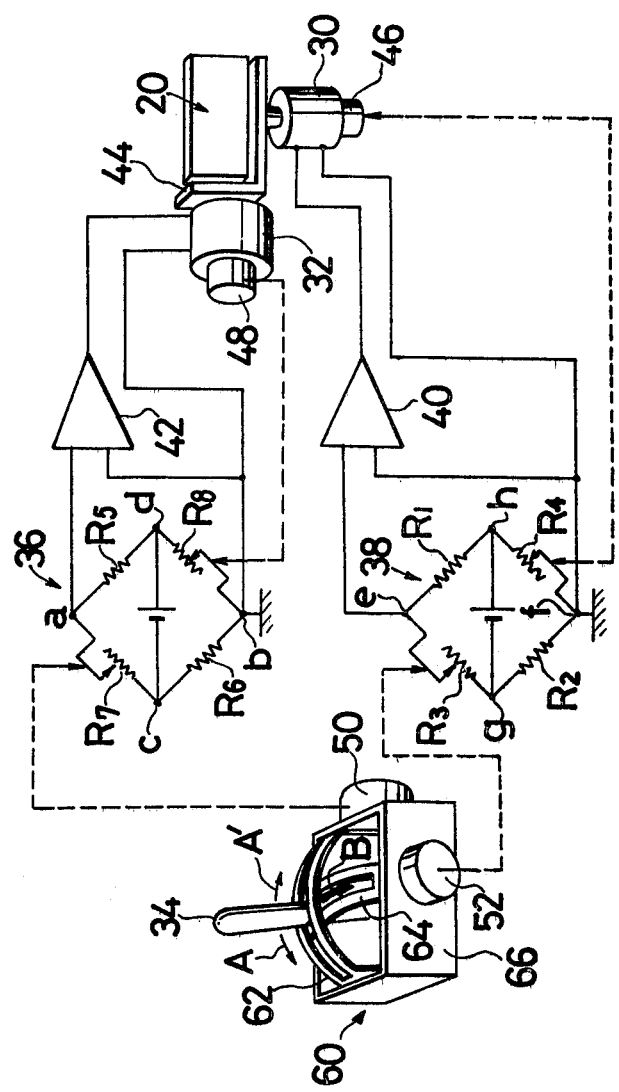
FIG. 4 is a circuit representation showing one embodiment of a servo-control for moving a plane reflector used in the apparatus shown in FIG. 1.

FIG. 4 is a circuit representation showing one embodiment of a servo-control used in the laser optical apparatus for operation under a microscope to effect positional control of the plane reflector. In a stick mechanism 60, guide plates 62 and 64, which are made from metal plates each formed with an elongated rectangular hole or opening therethrough, the metal plates being bended into a semi-circular configuration, are crossed at right angles to each other, one end thereof being rotatably mounted on a case 66 whereas the other end being mounted on shafts of potentiometers 50 and 52, respectively, A stick 34 is inserted into a hole at a point of intersection between the guide plates 62 and 64, and the lower end thereof is fixed in universal-joint fashion so that the upper end thereof can be moved freely by hands.

In bridge circuits 36 and 38, when the stick 34 is in the middle position, resistance values of resistors R1 to R8 are adjusted so that voltages between $a$ and $b$ and between $e$ and $f$, respectively, are zero (0). That is, equations $R1 \times R2 = R3 \times R4$ and $R5 \times R6 = R7 \times R8$ are established. When the stick 34 is displaced from the central position towards the direction A, the resistor R3 in the potentioneter 52 decreases to unbalance the bridge 38 and to produce a negative potential at point E. This negative potential is supplied to an amplifier 40 where it is amplified and then supplied to the servo-motor 30. When a negative voltage is applied to the servo-motor 30, the servo-motor 30 rotates rightwardly rotation of which is reduced in r.p.m. by a gear mechanism enclosed to slightly rotate the L-shaped supporting bed 44. As a consequence, the plane reflector 20 is slightly rotated in conjunction with the servo-motor mounted on the L-shaped supporting bed 44. A potentiometer 46 associated with the rotational shaft of the servo-motor 30 gradually increases in resistance $R4$ as the motor runs, and when the equation $R1 \times R2 = R3 \times R4$ is again to be established, the voltage between $e$ and $f$ assumes 0 to stop the servo-motor 30.

Conversely, when the stick 34 is displaced in the direction of A', the resistance R3 increases to produce a positive voltage at pont $e$ and as a result, the servo-motor 30 runs leftwardly. Then, the resistance R4 of the potentiometer 46 decreases to balance the bridge circuit 38 and at this time, the servo-motor 30 stops.

When the stick 34 is displaced from the central position to the direction B or B', the resistance R7 of the potentiometer 50 varies in value and the servo-motor 30 causes the plane reflector 20 to be slightly rotated about the axis z rightwardly or leftwardly. When the stick 34 is displaced in a direction other than the direction A—A' and B—B', two potentiometers 50 and 52 simultaneously run and the plane reflector 20 receives a combined motion of two slight rotations about the axes $x$ and $z$. In this manner, since the shaking motion of a single stick 34 and the shaking motion of the plane reflector 20 are in the ratio of 1 : 1, the operator may easily maneuver the apparatus. In other words, by employment of such an electric process as described above, it is not only capable of remote-controlling the apparatus but also of establishing a linear correspondence as previously mentioned between the shaking angle of the stick and the shaking angle of the plane reflector. It will further be noted in the control by means of the electric process that the sensitivity of the amplifier may be changed over by means of a switch whereby even when the stick is greatly displaced, the plane reflector is moved only in a small amount for the performance of precise operation. As is apparent from the foregoing, since two motors may be driven by a single stick (a maneuvering lever), operation is not only simple but remote control operation is possible to be made by extending a cord. For this reason, in the case where the operator holds operating instruments or the like in his hands, his assistant, while staying is a position away from the operator monitoring a television, can adjust the sight of a laser spot to the target position as instructed by the operator in a condition where disinfection is not required. Moreover, the present invention employs a method for moving the plane reflector in order to simultaneously reflect rays of light for observation and rays of laser, and accordingly, the range of vision and the laser spot will move at the same time and no displacement therebetween occurs. It should be noted that a glass plate, in which a circle of the same size as that of the laser spot is depicted about a point of crossed lines, may be inserted into the eyepiece system to thereby clearly indicate the position and the size of the laser spot, which eliminates the provision of guide light heretofore required.

What is claimed is:

1. A laser optical apparatus for operation under a microscope comprising: a laser beam introducing 45° reflector arranged between two optical axes so as not to impair the range of vision frontwardly of a binocular telescope for operation, a parabolic mirror with a surface displaced from an axis for condensing introduced beams of laser and serving as an objective lens of the microscope, a plane reflector for directing the condensed beams of laser and an optical axis of the microscope, and a servo mechanism for controlling the position of said plane reflector.

2. A laser optical apparatus as claimed in claim 1 wherein said servo mechanism includes a stick mechanism for instructing said servo mechanism to controlling the position of said plane reflector.

3. A laser optical apparatus as claimed in claim 1 wherein said servo mechanism includes bridge circuits for controlling the position of said plane reflector.

4. A laser optical apparatus as claimed in claim 1 wherein said servo mechanism includes an L-shaped bed for rotationally supporting said plane reflector, a first motor mounted on the vertical member of said L-shaped bed for rotating said plane reflector about a horizontal axis and a second motor rotationaly supporting the horizontal member of said L-shaped bed for rotating said L-shaped bed about a vertical axis.

* * * * *